United States Patent [19]

Sampson

[11] Patent Number: 4,929,236
[45] Date of Patent: May 29, 1990

[54] SNAP-LOCK FITTING CATHETER FOR AN IMPLANTABLE DEVICE

[75] Inventor: Edward J. Sampson, Carlisle, Mass.

[73] Assignee: Shiley Infusaid, Inc., Norwood, Mass.

[21] Appl. No.: 200,156

[22] Filed: May 26, 1988

[51] Int. Cl.⁵ .............................................. A61M 5/00
[52] U.S. Cl. ..................... 604/175; 604/283; 604/905; 128/912; 285/239; 285/921
[58] Field of Search ............ 604/175, 174, 283, 891.1, 604/905, 93; 128/912; 285/239–243, 255, 257, 258, 321, 323, 256, 921

[56] References Cited

U.S. PATENT DOCUMENTS

| | | | |
|---|---|---|---|
| 3,210,101 | 10/1965 | Bahr | 285/258 |
| 3,262,721 | 7/1966 | Knight | 285/242 |
| 4,632,435 | 12/1986 | Polyak | 285/243 |
| 4,692,146 | 9/1987 | Hilger | 604/93 |
| 4,704,103 | 11/1987 | Stöber et al. | 604/175 |
| 4,723,948 | 2/1988 | Clark et al. | 604/283 |
| 4,772,276 | 9/1988 | Wiita et al. | 604/283 |

FOREIGN PATENT DOCUMENTS

| | | | |
|---|---|---|---|
| 3048892 | 7/1982 | Fed. Rep. of Germany | 604/93 |
| 2586569 | 3/1987 | France | 604/61 |

Primary Examiner—Stephen C. Pellegrino
Assistant Examiner—Ralph Lewis
Attorney, Agent, or Firm—Sughrue, Mion, Zinn, Macpeak & Seas

[57] ABSTRACT

An implantable infusion device having a nipple outlet over which a catheter is fitted. A locking sleeve slidably mounted on the catheter to expand over the nipple and engage the housing. The locking action provides a sensory indication by noise of tactile sensation that locking has been achieved. Both single and double lumen devices employ the locking sleeve.

25 Claims, 2 Drawing Sheets

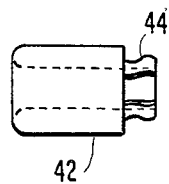
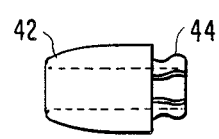
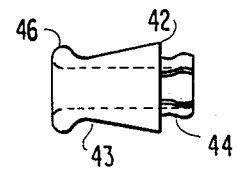
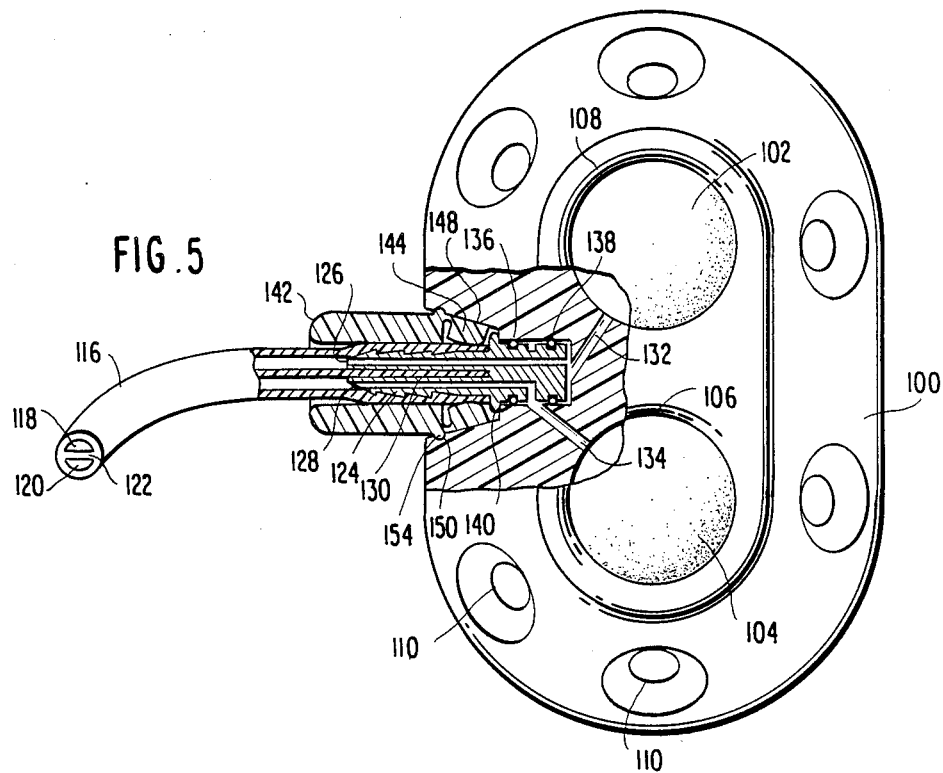
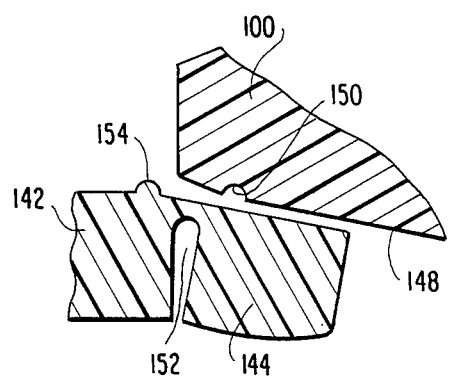

SNAP-LOCK FITTING CATHETER FOR AN IMPLANTABLE DEVICE

BACKGROUND OF THE INVENTION

This invention relates to an implantable device and in particular, to a vascular access device that is implanted subcutaneously. Within the prior art, a variety of implantable access devices are known and have been brought to the point of commercial acceptance. Typical of the commercially available devices is the INFUSAID Infus-a-Port TM. This device comprises, in its most basic form, an implantable port having access via a septum at a perpendicular angle to the skin via a needle. It has coupled to it a purcutaneous catheter extending generally at a right angle to the direction of needle access to the ports' inlet. These implantable devices typically use a variety of materials typically plastic such as PVC, Teflon (polytetrafluoroethylene), polyethylene polypropolyne, polyurethane, polycarbonate, polythermalsulfane, polysulphone, polyolenfin, nylon and the like. Additionally, silicon, and rubber may be employed while special components can be made of stainless steel or titanium.

An example, of a self-sealing implantable body utilizing an integral housing is described in U.S. Pat. 4,543,088. As illustrated therein, fluid communication between the internal reservoir and catheter (not shown) is via a passageway. While the catheter is not illustrated, the '088 patent mentions the use of rigid connectors which can be incorporated in the fluid passageWay to provide attachment of catheters and tubing to the implanted port.

An example of such rigid connection is found in U.S. Pat. No. 4,673,394. As illustrated and described in that patent, an implantable drug dispensing reservoir employs a twist-lock catheter coupled to a bayonet type connection. That is the implantable port has a T-slot into which a metallic flanged fitting is fitted and rotated into a locking arrangement. The '394 patent also employs a tab which is sutured into place against the base plate of the port to prevent detachment of the twist-lock connector from the port body. Another example is the screw-in lock assembly of U.S. Pat. No. 4,569,675.

Examples of press couplings of catheters into implantable ports are illustrated in and described in U.S. Pat. Nos. 4,445,495; 4,692,146; 4,710,167; and 4,710,174. In each, press fitting by frictional contact is used to hold the catheter in place with the port body. In the '146 patent, a metal nipple or tube may be used to prevent inadvertent puncture of the catheter itself. U.S. Pat. No. 4,464,178. also directed to an implantable port having an outlet catheter and employs a retainer having a pair of ears which engage matching voids in the reservoir. Such provides a positive locking and prevents the catheter from disengaging. However, problems in manufacture and replacement of the catheter are inherent in such a scheme. Another alternative of frictional yet detachably mounting a catheter to an implantable device is found in U.S. Pat. No. 4,581,020 which employs a tapered fluid connector which frictionally fits into an inlet to allow the catheter assembly to be detached.

U.S. Pat. No. 4,704,103 employs a catheter coupling using a coaxial elastomer clamping member that is deformed as a pressure sleeve is screwed into the port. To prevent the clamping member from crushing the catheter, a rigid hollow support projects from the outlet bore and the catheter slides over it. Thus, fluid communication is maintained as the catheter is clamped into position. Such a system is difficult to assemble in situ and contains a large number of components requiring surgeon time and precision.

One of the difficulties with these various prior art techniques is that they are difficult to engage, that is that the catheter is difficult to engage to the implanted port during an implantation procedure. That is, the implantation of such a drug delivery device should be as simple as possible to minimize patient trauma and the degree of skill required by the surgeon. In general, the reservoir is implanted subcutaneously at a location in the body cavity of the patient to provide needle access for infusion of medication. The catheter is then placed having one end at the drug delivery site with the second end to then be attached to the port. Given limited space, devices which require twist lock fittings and the like are difficult to connect in vivo and utilize in practice.

Moreover, in many of the devices which simply fit by means of pressure fitting, friction or the like, there is no indication that a complete and positive connection has been made. That is, no audible or tactile reference occurs indicating that an acceptable connection between the catheter and the port has been achieved. During the implantation procedure the surgeon must visually check or pull to determine whether the components have been coupled. Finally, devices which utilize machined parts and the like are more expensive to manufacture, have problems of material incompatibility, and present, to varying degrees, the problems of patient discomfort.

An overriding consideration is that the connection, in addition to providing the above requirements, establishes a fluid tight coupling between the catheter and the implantable reservoir.

SUMMARY OF THE INVENTION

Given the deficiencies of the prior art, it is an object of this invention to provide an improved catheter to implantable port coupling which provides an indication of a complete and operative connection between elements.

Yet another object of this invention is to provide an improved coupling between the catheter and an implantable port which is leak-tight and may be connected in a quick, simple manner.

Yet another object of this invention is to provide an improved catheter connection which is inexpensive to manufacture, and yet provides for removal and replacement of the catheter, if necessary.

These and other objects of this invention are accomplished by employing a snap-lock fitting which is provided axially on a catheter. The port has a barbed fitting which engages a snap-lock fitting on the catheter connector. The end of the catheter is first pushed onto the barbed fitting so that the catheter walls expand radially to provide a first coupling. The snap-lock fitting is then slid axially along the catheter until the fingers engage the port receptacle where they then compress radially inward. Further inward sliding of the snap-lock fitting causes local compression of the catheter around the barbs, enhancing the engagement of those elements. Also, this provides reserve material at the end should accidental pulling stretch the catheter. As the fingers radially expand to engage the rear shoulder portion of the barbed fitting thus providing a tactile as well as audible action indicating that a positive connection has been made. This connection technique may be used for both single and double lumen catheters.

This invention will be described in greater detail by referring to the attached drawings and a description of the preferred embodiment that follows.

BRIEF DESCRIPTION OF THE DRAWINGS

FIGS. 4A, 4B, 4C illustrate in a schematic view, three configurations of the snap-lock fitting in accordance with this invention;

FIG. 5 illustrates a second embodiment of this invention for use with a double lumen catheter; and FIG. 6 is a schematic view of the details of the engagement structure of the second embodiment of this invention.

DESCRIPTION OF THE PREFERRED EMBODIMENTS

Figure 1:
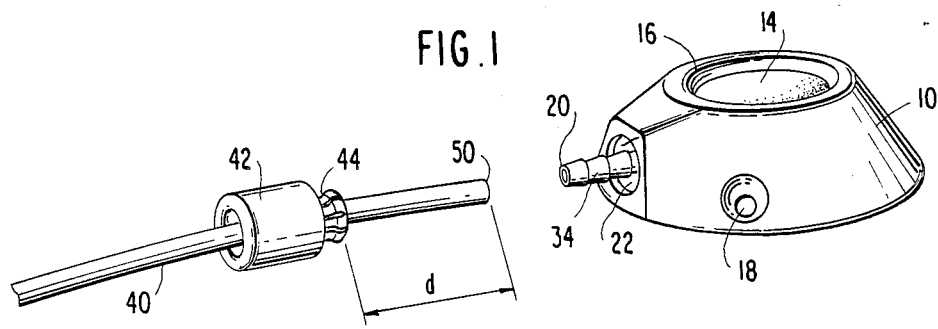
FIG. 1 is a schematic perspective view illustrating the basic components of a first embodiment of this invention prior to attachment.
Figure 2:
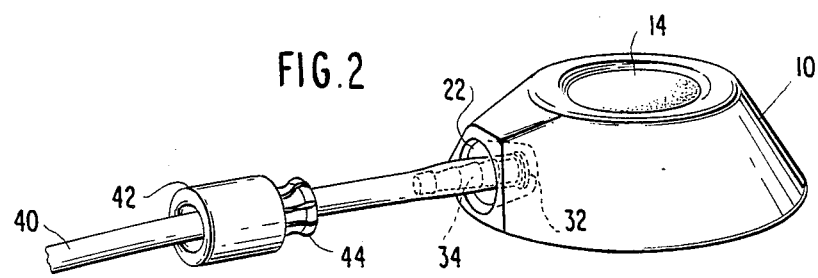
FIG. 2 is a schematic perspective view of the components of a first embodiment of this invention during an intermediate stage of attachment.
Figure 3:
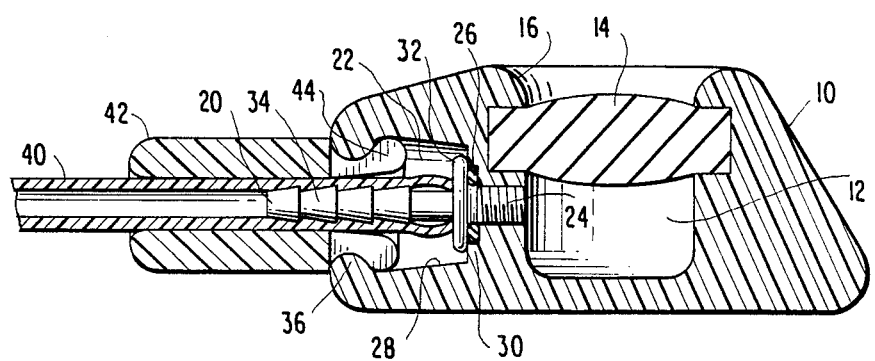
FIG. 3 is a schematic elevation view illustrating the components of a first embodiment of this invention in an engagement or locked position.

Referring now to FIGS. 1–3, the construction and assembly of a first embodiment of this invention pursuant to a first embodiment of the invention is depicted. The implantable device 10 may be similar to a commercial Infus-a-Port TM comprising a generally round shaped housing having a recess 12 forming a reservoir for retaining medication. A septum 14 is formed utilizing a self-sealing polymer such as silicon rubber or latex and is adapted to permit access utilizing a hypodermic needle to the reservoir 12. The housing 10 may also be formed of a compatible polymeric material. As illustrated in FIGS. 1 and 3, the septum 14 is press fitted into the housing 10, the housing having a generally rounded shoulder portion 16 to provide a palpable reference for locating the septum 14. That is, during charging of the reservoir 12, the technician physically locates the housing 10 by palpably sensing the location of the septum 14 as a function of determining the position of the annular shoulder 16.

FIG. 1 illustrates and attachment hole 18 which is used to suture the housing 10 into position within a body cavity. While one such suture hole 18 is illustrated, it will be understood that a plurality of such holes may be used to adequately anchor the device 10 in place.

An outlet from the reserVoir 12 as illustrated in FIG. 3 is formed by placing a barbed fitting or nipple 20 into an outlet cavity 22 in the housing 10. As illustrated in FIG. 3, the fitting 20 may have either a threaded section 24 or, not illustrated, another technique of anchoring a distal end of the fitting 20 in fluid contact to the reservoir 12. The outlet cavity 22 is shaped to have a generally cylindrical section 26 to receive an 0-ring disposed on the anchoring portion 24. A gradually tapered section 28 is used to receive the fingers, to be described herein, forming a portion of the snap-lock fitting. A wall 30 defines a positive stop by which a flange portion 32 of the nipple 20 seats to prevent impingement into the reservoir.

The outer portion of the barbed fitting 20 has a multiple flanged or barbed section 34 which, as illustrated in FIG. 3, protrudes beyond the outer wall of the housing 10. As illustrated, four annular barbs are used to "push-pull" lock onto the catheter. Further, as illustrated in FIG. 3, the barbs are of the same diameter The housing 10 has a generally annular shoulder 36 against which the fitting mounted on the catheter seats. It can be appreciated that the housing 10 having the various cavities can be formed by molding plastic with the septum 14 inserted during manufacture.

Referring now to FIG. 1, the catheter and the snap-lock fitting are illustrated. The catheter 40 is made from an inert material such as a silicone and is initially supplied in a suitable length so that one end, not illustrated, can be located at the drug delivery site. A snap-lock fitting 42 comprises a barrel section and an integral series of circumferentially disposed locking fingers 44. Each of the locking fingers 44 has an outwardly extending circumferential thickened portion and an inwardly positioned recessed portion. While the fitting 42 is illustrated in FIGS. 1–3 as generally cylindrical, other configurations may be used.

Referring to FIG. 4A, 4B and 4C, three alternatives are illustrated. FIG. 4A illustrates the generally cylindrical or barrel shaped snap-fitting while FIG. 4B illustrates a tapered fitting. Those devices are used in a situation where the snaplock connector will not be removed once it is coupled to the port 10. If removal or replacement is perceived, the fitting of FIG. 4C may be employed. As illustrated in that figure, the fitting has a generally extending circumferential recess 43 to allow finger grip on the connector 42. That is, the surgeon may physically grip in the region 43 and have a positive holding zone defined by the rearwardly extending shoulder portion 46. With one hand on the connector 42 and a second hand on the housing 10, the fitting may be physically separated from the housing.

The operation and installation of this device will now be described.

The housing 10 is implanted into the bodily cavity at a convenient site to allow for access via hypodermic needle. The catheter 40 is trimmed to its desired length at the proximal end once the distal end has been fixed at the infusion site. The snap-lock fitting 42 is located on the proximal end 50 of the catheter 40 [see FIG. 1], it being understood that the other end is that positioned at the infusion site. The snap-lock fitting is usually supplied mounted on the catheter but can be fitted by the surgeon if the catheter is replaced. A short length of the catheter having a distance (d) of approximately 0.5-1.0 inches protrudes beyond the fitting. The surgeon locates the tip of the nipple 20 by touch since it protrudes beyond the housing. The catheter 40 is then urged over the tip of the nipple 20 to engage the barbs 34. The catheter then, as illustrated in FIG. 2 is pushed up to the point where the flange and the barb fitting ends so that its outside wall deforms (see FIG. 3) and abuts against the flange 32. Thus fluid communication is established from the reservoir 12 through the barb fitting 20 and into the catheter 40.

Next, the snap-lock fitting 42 is slid up to the port body and snaps into the receptacle 22 of the port. As the fitting slides over the barbs contact with the shoulder 36 causes the fingers 44 to compress and then snap outward into locking engagement on the rear inward surface of the shoulder portion. The audible and tactile action of the spring fingers assures a good contact and at the same time provides an indication that an affirmative connection has been made. This placement of the snap-lock fitting also provides for stress relief of the catheter in case of bending on the barbed fitting. The action of sliding the snap-fitting over the barbs causes local compression and elongation of the catheter material. This material bunches up between the flange 32 and the fingers 44 providing a degree of reserve in case the catheter is accidentally pulled.

Should the catheter and its snap fitting require removal at a later date, the device as illustrated in FIG. 4 may be used in place of the generally cylindrical barrel 42. To effectuate removal, the surgeon grabs the snap fitting in the recess 43 and pries the fitting 42 apart while holding the port in the other hand thereby effectuating separation.

Referring now to FIGS. 5 and 6, a second embodiment of this invention is depicted. In FIG. 5 dual reservoir port 100 comprises an implantable port having a pair of self-sealing septums 102 and 104. As in the case of the embodiment of FIG. 1, each of the septums 102 and 104 is a self-sealing polymer such as silicon rubber or latex and adapted to permit access utilizing a hypodermic needle to the reservoirs, not illustrated. Housing 100 may also be formed of a compatible polymeric material. The septums are press-fitted into the housing with the housing having a pair of rounded shoulder portions 106, 108. The shoulder portions are used to provide a tactile reference for locating the respective septum. While illustrated in FIG. 5 as having a generally similar shape, the shoulder portions 106 and 108 may have different contours such as radius or squared-off or a point to provide the surgeon a point of reference for determining which septum is being accessed.

A series of suture holes 110 are provided on the periphery of the body for affixing the implantable device within a body cavity.

The embodiment of FIG. 5 therefore utilizes two distinct reservoirs which are coupled to discrete infusion sites by means of a double lumen catheter 116. This double lumen catheter has two parallel lumens, 118, 120 separated by means of an internal divider 122.

To accommodate the double lumen catheter 116, the barbed fitting or nipple of FIG. 1 must provide parallel flow channels. As illustrated in FIG. 5, this barbed fitting or nipple 124 has a pair of channels 126 and 128 to provide fluid communication with the channels 118 and 120 of the catheter 116. Additionally, a centrally disposed recess 130 is provided so that the divider 122 will engage the barbed fitting 124 so that alignment is established between the conduits 126 and 128 and the conduits 118 and 120 of the catheter.

The barbed fitting is anchored into the housing 100 so that fluid communication is maintained between conduits 132 and 134 which provide separate flow paths between each lumen of the catheter through the barbed fitting into a respective cavity in the implantable device. The nipple is secured within the housing, the pair of 0-rings 136, 138 are provided to isolate the flow paths 126 to conduit 132 and the flow path 128 into conduit 134. As in the case of the first embodiment, the nipple is anchored by means of a shoulder portion 140 which rests against an internal wall of the housing 100.

The snap-lock fitting 142 is different from that illustrated in the first embodiment. While it is an elongated cylindrical member which slides over the catheter 116, the fingers 144 are forced to move inward toward the catheter around the fitting gripping to provide a leak-tight connection. To achieve this inward movement, the internal wall 148 is radiused inward so that its circumference progressively decreases. The sleeve or snap lock fitting 142 has an inside diameter groove 152 which allows the fingers 144 to flex inward. At its outer periphery, as illustrated in FIG. 6, a small locking tooth 154 is provided to engage the annular detent or notch 150. The annular tooth 154 is physically compressed by plastic deformation to snap into the annular groove 150.

In operation, the assembly is provided in a manner generally similar to that of the first embodiment. A double lumen catheter is slid into engagement with the barbed fitting 124 with the divider 122 engaging the groove 130 for purposes of alignment. The proximal end of the catheter 116 abuts against the shoulder 140. Thus, fluid communication from both lumens of the catheter is initially established through the barbed fitting and conduits 132, 134 into each reservoir of the implantable device 100.

The sleeve 142 is then slid over the catheter 116. The fingers are urged inward by the wall 148 as the sleeve is inserted into the opening in the housing. Inward flexing of the fingers will close the groove 152. As the fingers 144 deform inwardly, they tend to compress the outer circumferential wall of the catheter against the barbs.

When the locking tooth 154 engages the notch 150, the audible and tactile clicking effect occurs locking sleeve 142 in place. Thus, snap-locking occurs. It is apparent that this snap-lock fitting opening arrangement used in FIG. 5 may also be employed relative to the single lumen catheter of FIG. 1.

While this invention has been described relative to a preferred embodiment and modifications of the snap-lock fitting it is apparent that modifications of this invention may be practiced without departing from the essential scope thereof.

Having described this invention, I claim:

1. An access device for implantation comprising;
a housing with at least a first reservoir therein, a self-sealing septum to provide subcutaneous access to said reservoir, an outlet in fluid communication with said reservoir and having a barbed nipple therein, a catheter having one end slidably mounted over said barbed nipple, and a locking sleeve having a through-hole for slidably mounting onto said catheter, said locking sleeve having a series of radially movable fingers which slide over said barbed nipple and engage said housing while compressing said catheter thereby locking said catheter and said sleeve to said housing and provide, upon engagement, a sensory indication that locking has been achieved.

2. The device of claim 1, wherein said outlet comprises an opening having a first cross-sectional area for receiving a first portion of said barbed nipple and a second cross-sectional area greater than said first cross-sectional area for receiving a second portion of said barbed nipple, said second cross-sectional area positioned inward from said outlet into said housing.

3. The device of claim 2, wherein said first portion of said barbed nipple comprises an anchoring portion to adhere said barbed nipple to said housing, said barbed nipple having a flange abutting said housing in the opening of said second area to prevent further insertion of said barbed nipple into said housing.

4. The device of claim 2, wherein said housing further comprises a shoulder section of reduced area to engage outer portions of said fingers when said locking sleeve slides over said barbed nipple.

5. The device of claim 4, wherein said outer portion of said fingers comprise a first inner section engaging an inside portion of said housing shoulder section and an adjacent second outer section of reduced area engaging an outer portion of said shoulder, whereby said fingers are compressed inward by said second outer section of said shoulder when said locking sleeve slides over said barbed nipple and then expand radially outward to engage said inside portion.

6. The device of claim 1, wherein said movable fingers are disposed circumferentially around said locking sleeve.

7. The device of claim 1, wherein said locking sleeve comprises a generally cylindrical outer section.

8. The device of claim 1, wherein said locking sleeve comprises a generally tapered conical outer section.

9. The device of claim 1, wherein said locking sleeve comprises a saddle shaped outer section having an annular recess to permit gripping.

10. The device of claim 1, wherein said catheter comprises a pair of lumens separated by an internal wall, said housing comprises a second reservoir, a second self-sealing septum and, fluid communication means coupling a respective lumen to a respective one of said first and second reservoirs.

11. The device of claim 10, wherein said barbed nipple comprises an elongated barbed member having conduits coupling respective lumens to said fluid communication means and an elongation slot engaging said internal wall of said catheter 12. The device of claim 1, wherein said outlet comprises a conical wall section, said radially movable fingers being compressed as said locking member slides over said barbed nipple.

13. The device of claim 12, wherein said conical wall section has a circumferential groove, said locking sleeve having an annular shoulder engaging said groove to lock said sleeve to said housing and providing a sensory indication that locking has occurred.

14. An implantable infusion device comprising:
a housing having an integral reservoir means defining a self-sealing septum for said reservoir said housing having an outlet opening, a barbed nipple section mounted in said outlet opening projecting outward and in fluid communication with said reservoir, a catheter fitted over said barbed nipple, and a locking sleeve slidably mounted over said catheter, said locking sleeve having radially movable fingers adapted to engage said housing to provide a detachable lock for said catheter, said fingers, upon engagement with said housing, providing a sensory indication that locking has been achieved.

15. The device of claim 14, wherein said outlet comprises an annular wall with a first section for receiving a first portion of said fingers and a second section positioned inward relative to first section for engaging a second portion of said fingers.

16. The device of claim 15, wherein said nipple section comprises an anchoring portion to adhere said barbed nipple section to said housing, said barbed nipple section having a flange abutting said housing in the opening to prevent further insertion of said barbed nipple section into said housing.

17. The device of claim 15, wherein said annular wall further comprises a groove section of reduced area, said sleeve having an annular shoulder to engage said groove section when said locking section slides over said barbed nipple section.

18. THe device of claim 15, wherein said fingers first portion comprise an outer section of reduced area engaging said housing first section and a second inner section of increased area engaging said housing second section.

19. The device of claim 15, wherein said annular wall first section is conical to compress said fingers and said second section comprises an annular groove, said fingers having an outer annular shoulder engaging said annular groove to lock said sleeve to said housing.

20. The device of claim 14, wherein said movable fingers are disposed circumferentially around said locking sleeve.

21. The device of claim 14, wherein said locking sleeve comprises a generally cylindrical outer section.

22. The device of claim 14, wherein said locking sleeve comprises a generally tapered conical outer section.

23. The device of claim 14, wherein said locking sleeve comprises a saddle shaped outer section having an annular recess to permit gripping.

24. The device of claim 14, wherein said catheter comprises a pair of lumens separated by an internal wall, said housing comprising a second reservoir and a second self-sealing septum and, fluid communication means coupling a respective lumen to a respective reservoir.

25. The device of claim 24, wherein said barbed nipple section comprises an elongated barbed member having conduits coupling respective lumens to said fluid communication means and an alignment slot engaging said internal wall of said catheter.

* * * * *